United States Patent [19]
Sharifian et al.

[11] Patent Number: 5,853,555
[45] Date of Patent: Dec. 29, 1998

[54] SYNTHESIS OF ONIUM HYDROXIDES FROM ONIUM SALTS

[75] Inventors: Hossein Sharifian; David R. Hulme, both of Austin, Tex.

[73] Assignee: Sachem, Inc., Austin, Tex.

[21] Appl. No.: 832,266

[22] Filed: Apr. 3, 1997

[51] Int. Cl.⁶ .................................................. B01D 61/44
[52] U.S. Cl. .......................................... 204/537; 204/535
[58] Field of Search ................................. 204/522, 537, 204/535; 205/431, 435, 436

[56] References Cited

U.S. PATENT DOCUMENTS

| | | | |
|---|---|---|---|
| 3,402,115 | 9/1968 | Campbell et al. | 204/180 |
| 3,523,068 | 8/1970 | Eisenbauer et al. | 204/72 |
| 4,391,680 | 7/1983 | Mani et al. | 204/98 |
| 4,394,226 | 7/1983 | Wade et al. | 204/72 |
| 4,578,161 | 3/1986 | Buonomo et al. | 204/102 |
| 4,740,281 | 4/1988 | Chlanda et al. | 204/151 |
| 4,904,357 | 2/1990 | Sharifian et al. | 204/73 R |
| 4,938,854 | 7/1990 | Sharifian et al. | 204/130 |
| 5,006,211 | 4/1991 | Paleologou et al. | 204/182.4 |
| 5,198,086 | 3/1993 | Chlanda et al. | 204/182.4 |
| 5,207,879 | 5/1993 | Butterworth | 204/182.4 |
| 5,240,579 | 8/1993 | Kedem | 204/182.4 |
| 5,250,159 | 10/1993 | Butterworth | 204/98 |
| 5,286,354 | 2/1994 | Bard et al. | 204/86 |
| 5,358,609 | 10/1994 | Drackett | 204/84 |
| 5,389,211 | 2/1995 | Sharifian et al. | 204/72 |
| 5,391,268 | 2/1995 | Kaczur et al. | 204/102 |
| 5,397,445 | 3/1995 | Umemura et al. | 204/182.4 |
| 5,447,610 | 9/1995 | Sharifian | 204/101 |

OTHER PUBLICATIONS

Genders, "Electochemical Salt Splitting", *Watts New: A Newsletter from The Electrosynthesis Company, Inc.,* vol. 1, No. 1, pp. 1–4, Sep. 1995.

Chang, "Conversion Of Ethylene Diamine Dihydrochloride Into Ethylenediamine By Electrodialytic Water–Splitting", *Journal of Applied Electrochemistry,* pp. 731–736, Nov. 1978.

*Primary Examiner*—Kathryn L. Gorgos
*Assistant Examiner*—Thomas H. Parsons
*Attorney, Agent, or Firm*—Renner, Otto, Boisselle & Sklar

[57] ABSTRACT

The present invention provides a process for preparing onium hydroxide from a corresponding onium salt and for purifying onium hydroxide including providing an electrochemical cell containing a cathode, an anode, a divider and a bipolar membrane, the bipolar membrane having an anion selective side facing the anode and a cation selective side facing the cathode, wherein the divider is positioned between the cathode and the bipolar membrane, and the bipolar membrane is positioned between the divider and the anode, thereby defining a feed compartment between the divider and the bipolar membrane, a recovery compartment between the divider and the cathode, and a water compartment between the bipolar membrane and the anode; charging a solution containing at least one of the onium salt and the onium hydroxide to be purified to the feed compartment; charging a liquid electrolyte to the other compartments; passing a current through the electrochemical cell to produce the onium hydroxide in the recovery compartment; and recovering the onium hydroxide from the recovery compartment.

31 Claims, 2 Drawing Sheets

5,853,555

SYNTHESIS OF ONIUM HYDROXIDES FROM ONIUM SALTS

FIELD OF THE INVENTION

This invention relates to a method of preparing and purifying onium hydroxides. More particularly, the invention relates to the method of preparing and purifying onium hydroxides such as quaternary ammonium hydroxides, quaternary phosphonium hydroxides, and tertiary sulfonium hydroxides from solutions containing the respective onium salts in an electrochemical cell which does not contain an anion selective membrane.

BACKGROUND OF THE INVENTION

Quaternary ammonium hydroxides such as tetramethylammonium hydroxide (TMAH) and tetraethylammonium hydroxide (TEAH) are strong organic bases that have been known for many years. Such quaternary ammonium hydroxides have found a variety of uses including use as a titrant for acids in organic solvents and as a supporting electrolyte in polarography. Aqueous solutions of quaternary ammonium hydroxides, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium and potassium, and halides such as chloride, bromide, iodide, etc. Particularly in recent years, there has been an increasing demand for quaternary ammonium hydroxides having a high purity.

Quaternary ammonium hydroxides such as TMAH and TEAH have been produced by various techniques. Generally, the quaternary ammonium hydroxides are manufactured by electrolyzing a salt of a quaternary ammonium compound in an electrochemical cell containing one or more cation-exchange membranes. The quaternary ammonium salts used in such preparations include halogenated salts, carboxylate salts, carbonate salts and sulfate salts.

Electrochemical cells use electrical current as a means to cause the movement of ions in solution. Among the prior art patents which describe the preparation of quaternary ammonium hydroxides by electrolyzing a salt of a quaternary ammonium compound are U.S. Pat. No. 4,578,161 (Buonomo et al); U.S. Pat. No. 4,394,226 (Wade et al); U.S. Pat. No. 3,523,068 (Eisenhauer et al); and U.S. Pat. No. 3,402,115 (Campbell et al). Electrodialysis processes are known in the art and are typically carried out in a stack arrangement comprising a plurality of flat sheet membranes. A stack consists of electrodes (anode and cathode) at either end and a series of membranes and gaskets which are open in the middle to form a multiplicity of compartments separated by the membranes. Usually, a separate solution is supplied to the compartments containing the electrodes, and special membranes may be placed next to the electrode containing compartments in order to prevent mixing of the process steams with the electrode streams. The stack between the electrode compartments comprises an assembly of repeating series of units of different membranes with solution compartments between adjacent membranes. This repeating unit is called a unit cell. Each unit cell is arranged to provide a plurality of parallel flow paths or channels therebetween. Solution is typically supplied to the compartments by internal manifolds formed as a part of the gaskets or by a combination of internal and external manifolds. The stacks can include more than one type of unit cell, and streams may be fed from one stack to another in order to optimize process efficiency.

Treatment of aqueous salt streams by electrodialysis to form acid and/or base from the salt is known. The aqueous salt stream is fed to an electrodialytic water-splitting apparatus which comprises an electrodialysis stack and a means for electrodialytically splitting water. A useful means to split water to $H^+$ and $OH^-$ is a bipolar membrane. Bipolar membranes are comprised of an anion-selective layer and a cation-selective layer of ion exchange material. In order for the membrane to function as a water splitter, the layers must be arranged so that the anion layer in each membrane is closer to the anode than the cation layer. An electric current passed through the membrane in this configuration will cause water splitting with hydroxyl ions being produced on the anode side and a corresponding number of hydrogen ions being produced on the cathode side of the membrane. The disassociated salt cations pass through cation selective membranes and move toward the cathode, and the disassociated salt anions pass through the anion selective membrane and move toward the anode.

Electrodialytic water splitting in a two-compartment cell has been disclosed in, for example, U.S. Pat. No. 4,391,680 relating to the generation of strongly acidified sodium chloride and aqueous sodium hydroxide from aqueous sodium chloride. Three compartment electrodialytic water splitters are disclosed to be comprised of alternating bipolar, anion and cation exchange membranes in, for example, U.S. Pat. No. 4,740,281.

U.S. Pat. No. 5,397,445 describes various electrodialytic configurations employing bipolar, anionic and cationic membranes for producing an acid and/or an alkali metal hydroxide from a neutral salt. U.S. Pat. No. 5,198,086 also describes various configurations or electrodialytically converting salt, the salt of a strong base and a weak acid to a base with improved purity.

SUMMARY OF THE INVENTION

In one embodiment, the present invention relates to a process for preparing onium hydroxide from a corresponding onium salt and for purifying onium hydroxide including providing an electrochemical cell containing a cathode, an anode, a divider and a bipolar membrane, the bipolar membrane having an anion selective side facing the anode and a cation selective side facing the cathode, wherein the divider is positioned between the cathode and the bipolar membrane, and the bipolar membrane is positioned between the divider and the anode, thereby defining a feed compartment between the divider and the bipolar membrane, a recovery compartment between the divider and the cathode, and a water compartment between the bipolar membrane and the anode; charging a solution containing at least one of the onium salt and the onium hydroxide to be purified to the feed compartment; charging a liquid electrolyte to the other compartments; passing a current through the electrochemical cell to produce the onium hydroxide in the recovery compartment; and recovering the onium hydroxide from the recovery compartment.

In another embodiment, the present invention relates to a process for preparing an onium hydroxide from a corresponding onium salt including providing an electrochemical cell containing a cathode, an anode, a cation selective membrane and a bipolar membrane, the bipolar membrane having an anion selective side facing the anode and a cation selective side facing the cathode, wherein the cation selective membrane is positioned between the cathode and the bipolar membrane, and the bipolar membrane is positioned between the cation selective membrane and the anode, thereby defining a feed compartment between the cation selective membrane and the bipolar membrane, a recovery compartment between the cation selective membrane and the cathode, and a water compartment between the bipolar membrane and the anode; charging a solution containing the onium salt to the feed compartment; charging a liquid electrolyte to the other compartments; passing a current through the electrochemical cell to produce the onium hydroxide in the recovery compartment; and recovering the onium hydroxide from the recovery compartment.

In yet another embodiment, the present invention relates to a process for purifying an onium hydroxide solution including providing an electrochemical cell containing a cathode, an anode, a cation selective and a bipolar membrane, the bipolar membrane having an anion selective side facing the anode and a cation selective side facing the cathode, wherein the cation selective membrane is positioned between the cathode and the bipolar membrane, and the bipolar membrane is positioned between the cation selective membrane and the anode, thereby defining a feed compartment between the cation selective membrane and the bipolar membrane, a recovery compartment between the cation selective membrane and the cathode, and a water compartment between the bipolar membrane and the anode; charging the onium hydroxide solution to the feed compartment; charging a liquid electrolyte to the other compartments; passing a current through the electrochemical cell to regenerate onium hydroxide in the recovery compartment; and recovering a purified onium hydroxide solution from the recovery compartment.

In a number of other embodiments, the inventive processes further include the use of an additional electrochemical cell, a diffusion dialysis cell, an ion exchange system or a distillation apparatus. As a result of the present invention, extremely pure and/or concentrated solutions of onium hydroxides are obtainable at low cost and high efficiency.

DESCRIPTION OF THE PREFERRED EMBODIMENTS

Figure 1:
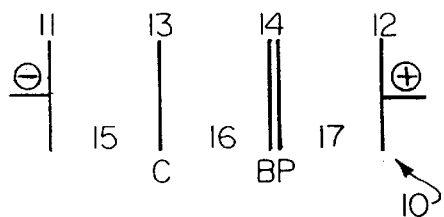
FIG. 1 is a schematic representation of a three compartment electrochemical cell containing one unit cell useful for preparing and/or purifying onium hydroxides in accordance with the invention.

The onium hydroxides which are prepared and/or purified in accordance with the process of the present invention are derived from the corresponding onium salts. The onium salts may generally be characterized by the formula $$A^+X^-$$

wherein $A^+$ is an onium cation and $X^-$ is an anion of an acid such as a halide ion, a sulfate, hydrogen sulfate or alkylsulfate anion, a carboxylate anion, a nitrate anion, a carbonate, bicarbonate or alkyl carbonate anion, a phosphate, hydrogen phosphate or dihydrogen phosphate anion, etc. Halide, sulfate, formate and carbonate anions are preferred, and halide anions are most preferred. The halide ions include chloride, bromide and iodide ions. An example of an alkyl sulfate anion is methyl sulfate ($CH_3SO_4^-$), and examples of carboxylic acid anions include the formate, acetate and oxalate anions. An onium hydroxide is represented by the formula when X is a hydroxide group.

In one preferred embodiment of the present invention, the onium salts are characterized by the above formula where $A^+$ is a quaternary ammonium, quaternary phosphonium or a tertiary sulfonium cation.

The quaternary ammonium and quaternary phosphonium salts may be characterized by the formula

wherein A is a nitrogen or phosphorus atom, $X^-$ is an anion of an acid as described above, y is a number equal to the valence of X, and $R^1$, $R^2$, $R^3$ and $R^4$ are each independently alkyl groups containing from 1 to about 20 carbon atoms, hydroxyalkyl or alkoxyalkyl groups containing from 2 to about 20 carbon atoms, aryl groups, or hydroxyaryl groups, or $R^1$ and $R^2$ together with A may form a heterocyclic group provided that if the heterocyclic group contains a C=A group, $R^3$ is the second bond.

The alkyl groups may be linear or branched, and specific examples of alkyl groups containing from 1 to 20 carbon atoms include methyl, ethyl, propyl, butyl, pentyl, hexyl, heptyl, octyl, isooctyl, nonyl, octyl, decyl, isodecyl, dodecyl, tridecyl, isotridecyl, hexadecyl and octadecyl groups. $R^1$, $R^2$, $R^3$ and $R^4$ also may be hydroxyalkyl groups such as hydroxyethyl and the various isomers of hydroxypropyl, hydroxybutyl, hydroxypentyl, etc. In one preferred embodiment, the R groups are independently alkyl groups containing one to ten carbon atoms and hydroxyalkyl groups containing from two to three carbon atoms. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

Examples of quaternary ammonium halides representative of Formula I which can be treated in accordance with the process of the present invention to form quaternary ammonium hydroxides include tetramethylammonium chloride, tetramethylammonium bromide, tetraethylammonium chloride, tetraethylammonium bromide, tetrapropylammonium bromide, tetrabutylammonium bromide, tetra-n-octylammonium bromide, trimethylhydroxyethylammonium chloride, trimethylmethoxyethylammonium chloride, dimethyldihydroxyethylammonium chloride, methyltrihydroxyethylammonium chloride, phenyltrimethylammonium chloride, phenyltriethylammonium chloride, benzyltrimethylammonium chloride, benzyltriethylammonium chloride, dimethylpyrolidinium bromide, dimethylpiperidinium bromide, diisopropylimidazolinium bromide, N-alkylpyridinium bromide, etc. The corresponding quaternary ammonium sulfate, nitrate, carbonate, alkyl carbonate, bicarbonate, phosphate, formate, acetate and oxalate salts also can be used.

Examples of quaternary phosphonium halides representative of Formula I which can be used in the process of the present invention to form quaternary phosphonium hydroxides include tetramethylphosphonium bromide, tetraethylphosphonium bromide, tetrapropylphosphonium bromide, tetrabutylphosphonium bromide, trimethylhydroxyethylphosphonium bromide, dimethyidihydroxyethylphosphonium bromide, methyltrihydroxyethylphosphonium bromide, phenyltrimethylphosphonium bromide, phenyltriethylphosphonium bromide and benzyltrimethylphosphonium bromide. The corresponding chloride, sulfate, nitrate, phosphate, carbonate, alkyl carbonate, bicarbonate, formate, acetate and oxalate salts also can be converted to the corresponding hydroxides.

In another embodiment, the tertiary sulfonium salts which can be used in accordance with this invention to form tertiary sulfonium hydroxides may be represented by the formula

wherein $X^-$ is an anion of an acid as described above, y is a number equal to the valence of X, and $R^1$, $R^2$ and $R^3$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R^1$ and $R^2$ together with S may form a heterocyclic group provided that if the heterocyclic group contains a C=S group, $R^3$ is the second bond.

Examples of the halides represented by Formula II include trimethylsulfonium chloride, trimethylsulfonium bromide, triethylsulfonium bromide, tripropylsulfonium bromide, etc. The corresponding chloride, sulfate, nitrate, phosphate, carbonate, alkyl carbonate, bicarbonate, formate, acetate and oxalate salts also can be converted to the corresponding hydroxides.

In one preferred embodiment, the quaternary ammonium salt is represented by the formula

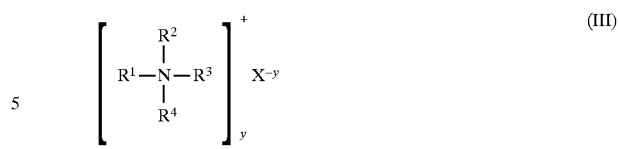

wherein $R^1$, $R^2$, $R^3$ and $R^4$ are each independently alkyl groups containing from 1 to 10 carbon atoms, hydroxyalkyl or alkoxyalkyl groups containing from 2 to about 10 carbon atoms, aryl groups or hydroxyaryl groups, X is an anion of an acid, and y is a number equal to the valence of X.

Specific examples of alkyl groups containing from 1 to 10 carbon atoms include methyl, ethyl, propyl, butyl, pentyl, hexyl, heptyl, octyl, nonyl, and decyl groups. $R^1$, $R^2$, $R^3$ and $R^4$ also may be hydroxyalkyl groups such as hydroxyethyl and the various isomers of hydroxypropyl, hydroxybutyl, hydroxypentyl, etc. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

Specific examples of the anion $X^-$ include the halide anions such as fluoride, chloride, bromide and iodide, sulfate anions, nitrate anions, formate anions, acetate anions, oxalate anions, alkyl carbonate, carbonate and bicarbonate anions, etc. The process of the present invention is particularly useful when the salt is a halide, carbonate and formate.

In one preferred embodiment, the R groups are alkyl groups containing 1 to 4 carbon atoms and hydroxyalkyl groups containing from 2 to 4 carbon atoms. Most often, the quaternary ammonium salts treated in accordance with the process of the present invention will be tetramethylammonium chloride, tetraethylammonium chloride, tetra-n-propylammonium chloride or tetra-n-butylammonium chloride.

In accordance with the process of the present invention, the onium salts such as those described above are converted to onium hydroxides and/or the onium hydroxides are purified in at least one electrochemical cell. In certain embodiments, especially embodiments where onium hydroxide is prepared from a corresponding onium salt, at least two electrochemical cells or one electrochemical cell and one diffusion dialysis cell or an electrochemical cell and a distillation apparatus or an electrochemical cell and an ion exchange system are used. In embodiments involving two cells, the second electrochemical cell or the diffusion dialysis cell is a secondary cell and the first electrochemical cell is a primary cell. The conversion or purification may be by electrolysis in an electrolytic cell or by electrodialysis in an electrodialytic cell or by diffusion dialysis technique in a diffusion dialysis cell.

The electrochemical cells generally comprise an anode, a cathode, and one or more unit cells assembled for operational positioning between the anode and the cathode. A number of electrolytic and electrodialytic cells containing various unit cells and multiple unit cells are described herein which are useful in the process of the present invention. Multiple unit cells may be defined by a number of compartments between an anode and a cathode (see, for example, FIGS. 3 and 10), or multiple unit cells may be defined by a number of compartments including an anode and cathode (see, for example, FIGS. 4, 5 and 8). Multiple unit cells including an anode and cathode may take a monopolar configuration (see, for example, FIGS. 5 and 8), or a bipolar configuration (see, for example, FIG. 4). There is no particular limit to the number of unit cells which can be used. Nevertheless, in one embodiment, electrochemical cells which are used according to the present invention contain from 1 to about 25 unit cells, and preferably from 1 to about 10 unit cells.

The unit cells may comprise three or more compartments defined by the anode, cathode, one or more bipolar membranes and one or more dividers or separators which may be (1) nonionic microporous diffusion barriers such as screens, filters, diaphragms, etc., of controlled pore size or pore size distribution allowing certain ions to pass through the divider or separator, or (2) ionic dividers or separators such as cation selective membranes which are preferred since their use generally results in the production of onium hydroxides of higher purity and in higher yield. The various dividers useful in the electrochemical cells used in the invention are described more fully below. In embodiments involving the use of two or more electrochemical cells, the ionic dividers or separators of the second electrochemical cell may also be anion selective membranes.

In a preferred embodiment, the primary electrochemical cell does not contains an anion selective membrane. Eliminating the requirement of an anion selective membrane from the primary electrochemical cell provides a more efficient, less complicated and less expensive process compared to those processes heretofore known.

In one embodiment, a unit cell of the primary electrochemical cells contains at least three compartments defined by, in sequence beginning at the anode, a bipolar membrane and a divider, the bipolar membrane having an anion selective side facing the anode and a cation selective side facing the cathode. In embodiments where the primary electrochemical cells contain at least three compartments, the three compartments generally include a feed compartment, a water compartment and a recovery compartment. Optionally, primary electrochemical cells may contain at least one purge compartment and/or a buffer compartment. In certain embodiments, an electrochemical cell may have two or more of each of the compartments described above. In other embodiments, the electrochemical cell may have two or more of any of the compartments listed above. For example, in one embodiment, an electrochemical cell may have two feed compartments, one water compartment and two recovery compartments.

In some embodiments, a second electrochemical cell is used. The second electrochemical cells contain an anode, a cathode, and at least three compartments, the three compartments generally including at least a feed-recovery compartment, a waste compartment and one or more of an anolyte compartment and a catholyte compartment. The compartments of the second electrochemical cell are defined by the anode, cathode, one or more bipolar membranes and one or more dividers or separators including cation selective membranes and anion selective membranes. In one embodiment, the secondary electrochemical cell does not contain a cation selective membrane.

In other embodiments, a diffusion dialysis cell is used in addition to the electrochemical cell. A diffusion dialysis cell generally includes at least two compartments; namely, a charge-recovery compartment and a permeate compartment. The two compartments of the diffusion dialysis cell are separated by a diffusion dialysis membrane. Diffusion dialysis cells are advantageous in that there is no need to apply a current to the cell.

In still other embodiments, either an ion exchange system or a distillation apparatus is used in addition to the electrochemical cell. The ion exchange system preferably comprises a weak or strong anionic exchange resin.

A solution is charged to each compartment of each cell. The solution may be an aqueous solution or an organic solution or combinations thereof. In a preferred embodiment, the solution charged into each compartment is an aqueous solution. When water is used, it is preferable to use deionized water although tap water may also be used. Organic solutions include alcohols, glycols and other relatively polar organic liquids.

The solution charged into the feed compartment contains the onium hydroxide to be purified and/or the onium salt to be converted at certain concentrations. The concentration of the onium cation initially charged into the feed compartment is in the range from about 0.01M to about 2M. In another embodiment, the concentration of the onium cation in the solution charged into the feed compartment is from about 0.1M to about 1.5M. In electrochemical cells containing two or more feed compartments, the concentrations of the onium salt and onium hydroxide in the solutions charged into the feed compartments may be the same or different for each feed compartment. The concentration of the onium salt and/or onium hydroxide in the solution charged to the cell is from about 3% to about 55% by weight and more often between 5% and 40% by weight. The feed compartment, as the term implies, holds the solution containing the onium hydroxide which is to be purified and/or the onium salt to be converted by the electrochemical cell.

The water compartment contains a solution of a liquid electrolyte at a certain concentration. The liquid electrolyte contains an ionic compound and at least one of an aqueous liquid and an organic liquid. The water compartment containing a liquid electrolyte serves to maintain conductivity and enable lower operating cell voltages. An ionic compound is a chemical compound that fully or partially ionizes in solution, such as an electrolyte. Examples of ionic compounds include salts, metal salts and acids or any compound which forms an anion and cation when dissolved in solution. In a preferred embodiment, the ionic compound is the same as the onium salt and/or onium hydroxide charged into the feed compartment. In another preferred embodiment, the ionic compound is a mineral acid such as nitric acid, sulfuric acid or phosphoric acid and the liquid electrolyte is a dilute solution of a mineral acid. In another embodiment, the ionic compound is different from the onium salt and/or onium hydroxide charged into the feed compartment. The concentration of the ionic compound in the water compartment is in the range from about 0.01M to about 2M. In a preferred embodiment, the concentration is from about 0.05M to about 1.5M. And in a most preferred embodiment, the concentration is from about 0.1M to about 1M. In electrochemical cells containing two or more water compartments, the concentrations of the ionic compound in the solutions charged into the water compartments may be the same or different for each water compartment.

The recovery compartment initially is charged with a solution of a liquid electrolyte and preferably the same solution charged to the water compartment. After passing a current through the electrochemical cell, the onium hydroxide may be recovered or otherwise obtained from the recovery compartment at a certain concentration. After passing a current through the electrochemical cell, the concentration of the onium hydroxide in the recovery compartment is generally higher than the concentration of the onium hydroxide initially charged into the feed compartment. In one embodiment, the concentration of the onium hydroxide in the recovery compartment is above about 1M. In another embodiment, the concentration of the onium hydroxide in the recovery compartment is above about 1.5M. In a preferred embodiment, the concentration of the onium hydroxide in the recovery compartment is above about 2M. In electrochemical cells containing two or more recovery compartments, the concentrations of the onium hydroxide in the solutions recovered from the recovery compartments may be the same or different for each recovery compartment.

The purge compartment initially is charged with a solution of a liquid electrolyte and preferably the same solution charged to the recovery compartment. After passing a current through the electrochemical cell, the onium cation passes through the purge compartment in embodiments where a purge compartment is used. Since most undesirable compounds do not pass through the purge compartment, the purge compartment serves to The buffer compartment initially is charged with a solution of a liquid electrolyte and preferably the same solution charged to the recovery compartment. After passing a current through the electrochemical cell, impurities sometimes contaminate the recovery compartment. The buffer compartment tends to attract impurities as the impurities are sometimes prone to cross bipolar membranes. Accordingly, the buffer compartment serves to further purify the onium hydroxide.

In certain circumstances, an undesirable amount of acid may accumulate in the feed compartment. Excess acid in the feed compartment can lessen the current efficiency since hydronium ions may migrate from the feed compartment to the recovery compartment. In these instances, solution from the feed compartment may be transferred to a secondary cell, such as a second electrochemical cell or a diffusion dialysis cell, to an ion exchange system (ion exchange techniques are known) or to a distillation apparatus (distillation techniques are known). In these embodiments, the electrochemical cell containing the feed compartment originally charged with the onium salt and/or onium hydroxide solution is referred to as the primary electrochemical cell. The secondary cells, the ion exchange system and the distillation apparatus serve to remove some or all of the undesirable amounts of acid from the solution originally charged to the feed compartment.

After a desired amount of acid has been removed, a solution containing the onium salt and a reduced amount of acid may be recovered and transferred back to the feed compartment of the primary electrochemical cell. In embodiments where the onium salt and/or onium hydroxide solution contains an onium sulfate, an onium nitrate or onium halide such as onium chloride, it is preferable to employ the use of secondary cells to remove excess acid that may form. In embodiments where the onium salt and/or onium hydroxide solution contains an onium formate, it is preferable to employ the use of a distillation apparatus to remove excess formic acid that may form. In embodiments where the onium salt and/or onium hydroxide solution contains an onium carbonate, onium bicarbonate or an onium alkyl carbonate, a secondary electrochemical cell or a diffusion dialysis cell is not needed to remove impurities such as $CO_2$ from the solution.

In embodiments involving the use of a second electrochemical cell, the solution charged into the feed-recovery compartment contains the onium salt to be converted at certain concentrations and typically an undesirable amount of acid. The concentration of the onium cation initially charged into the feed-recovery compartment is in the range from about 0.01M to about 2M. In another embodiment, the concentration of the onium cation in the solution charged into the feed-recovery compartment is from about 0.1M to about 1.5M. In the second electrochemical cell containing two or more feed-recovery compartments, the concentrations of the onium salt in the solutions charged into the feed-recovery compartments may be the same or different for each feed-recovery compartment. After passing a current through the second electrochemical cell, acid and/or undesirable anions pass to the waste compartment thereby increasing the pH of the solution in the feed-recovery compartment. The solution recovered from the feed-recovery compartment is then transferred back to the feed compartment of the primary electrochemical cell.

The waste compartment initially is charged with a solution of a liquid electrolyte. After passing a current through the electrochemical cell, acid and/or impurities may be recovered or otherwise obtained from the waste compartment at a certain concentration. Impurities may be disposed of while acid may be reused where appropriate. In one embodiment, the concentration of the acid in the waste compartment is above about 5M. In another embodiment, the concentration of the acid in the waste compartment is above about 3M. In a preferred embodiment, the concentration of the acid in the waste compartment is above about 1M. In secondary electrochemical cells containing two or more waste compartments, the concentrations of the acid and/or impurities in the solutions recovered from the waste compartments may be the same or different for each waste compartment.

The anolyte and catholyte compartments initially are charged with a solution of a liquid electrolyte and preferably the same solution charged to the recovery compartment of the primary electrochemical cell. The anolyte and catholyte compartments containing a liquid electrolyte serve to maintain conductivity and enable lower operating cell voltages.

In embodiments involving the use of a diffusion dialysis cell, the solution charged into the charge-recovery compartment contains the onium salt to be converted at certain concentrations and typically an undesirable amount of acid. The concentration of the onium cation initially charged into the charge-recovery compartment is in the range from about 0.01M to about 2M. In another embodiment, the concentration of the onium cation in the solution charged into the charge-recovery compartment is from about 0.1M to about 1.5M.

An aqueous solution, preferably containing only deionized water, or an organic solution, preferably containing no solutes, is charged to the permeate compartment of the diffusion dialysis cell. The solution charged to the permeate compartment may be recycled in order to remove acid, impurities or other compounds so as to maintain the concentration gradient which, in turn, promotes the passage of compounds across the diffusion dialysis membrane.

Over time due to the concentration gradient, acid and/or undesirable anions pass to the permeate compartment thereby increasing the pH of the solution in the charge-recovery compartment. The solution recovered from the charge-recovery compartment is then transferred back to the feed compartment of the primary electrochemical cell.

In embodiments involving the use of an ion exchange system or a distillation apparatus, solution containing an onium salt and typically an undesirable amount of acid is transferred from the feed compartment of the electrochemical cell, treated (passed through the ion exchange system or distilled), and returned to the feed compartment containing a reduced amount of acid and/or other impurities.

Several embodiments of electrochemical cells which may be used in the invention will be described with reference to the figures. Although numerous embodiments of various electrochemical cells are described in the figures, it will be readily apparent to those skilled in the art that numerous embodiments not specifically described in the figures exist within the scope of the invention.

An embodiment of an electrochemical cell is illustrated in FIG. 1, which is a schematic representation of an electrochemical cell 10 containing a cathode 11, an anode 12 and a unit cell containing in sequence beginning at the cathode 11, a cation selective membrane 13, and a bipolar membrane 14. The bipolar membrane 14 has an anion selective side (not shown) facing the anode and a cation selective side (not shown) facing the cathode. The electrochemical cell 10 contains three compartments; namely, a feed compartment 16, a recovery compartment and a water compartment 17.

In operation of the electrochemical cell illustrated in FIG. 1, a solution containing a liquid electrolyte is charged to the water compartment 17 and the recovery compartment 15. A solution containing an onium hydroxide and/or an onium salt is fed to the feed compartment 16. An electrical potential is established and maintained between the anode and the cathode to produce a flow of current across the cell whereupon the onium cations are attracted toward the cathode and pass through the cation selective membrane 13 into the recovery compartment 15. The onium cations combine with hydroxide ions formed at the cathode to produce the desired onium hydroxide. Impurities such as chloride ion, formate anions and carbonate anions are attracted to the anode and thus remain in the feed compartment 16. Purified onium hydroxide is formed and recovered from the recovery compartment 15.

Figure 2:
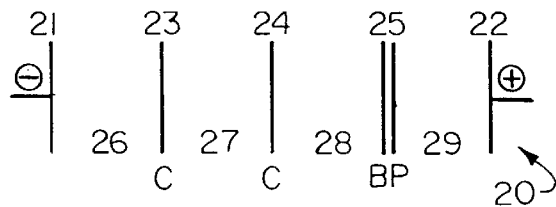
FIG. 2 is a schematic representation of a four compartment electrolytic cell containing one unit cell in accordance with the invention.

An embodiment of an electrochemical cell is illustrated in FIG. 2, which is a schematic representation of an electrochemical cell 20 containing a cathode 21, an anode 22 and a unit cell containing in sequence beginning at the cathode 21, a first cation selective membrane 23, a second cation selective membrane 24, and a bipolar membrane 25. The bipolar membrane 25 has an anion selective side (not shown) facing the anode and a cation selective side (not shown) facing the cathode. The electrochemical cell 20 contains four compartments; namely, a feed compartment 28, a purge compartment 27, a recovery compartment 26 and a water compartment 29.

In operation of the electrochemical cell illustrated in FIG. 2, a solution containing a liquid electrolyte is charged to the water compartment 29, the purge compartment 27, and the recovery compartment 26. A solution containing an onium hydroxide and/or an onium salt is fed to the feed compartment 28. An electrical potential is established and maintained between the anode and the cathode to produce a flow of current across the cell whereupon the onium cations are attracted toward the cathode and pass through the purge compartment and cation selective membranes 24 and 23 into the recovery compartment 26. The onium cations combine with hydroxide ions formed at the cathode to produce the desired onium hydroxide. Impurities such as chloride ion, formate anions and carbonate anions are attracted to the anode and thus remain in the feed compartment 28. Purified onium hydroxide is formed and recovered from the recovery compartment 26.

Figure 3:
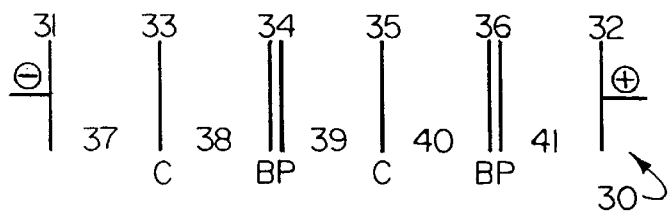
FIG. 3 is a schematic representation of an electrodialytic cell containing a stack of two units of the unit cell of FIG. 1 in accordance with the invention.

An embodiment of an electrochemical cell is illustrated in FIG. 3, which is a schematic representation of an electrochemical cell 30 containing a cathode 31, an anode 32 and a polyunit cell containing in sequence beginning at the cathode 31, a first cation selective membrane 33, a first bipolar membrane 34, a second cation selective membrane 35, and a second bipolar membrane 36. The bipolar membranes 34 and 36 have an anion selective side (not shown) facing the anode and a cation selective side (not shown) facing the cathode. The electrochemical cell 30 contains five compartments; namely, a first feed compartment 38, a first recovery compartment 37, a second feed compartment 40, a second recovery compartment 39 and a water compartment 41.

In operation of the electrochemical cell illustrated in FIG. 3, a solution containing a liquid electrolyte is charged to the water compartment 41 and the recovery compartments 37 and 39. A solution containing an onium hydroxide and/or an onium salt is fed to the feed compartments 38 and 40. An electrical potential is established and maintained between the anode and the cathode to produce a flow of current across the cell whereupon the onium cations are attracted toward the cathode and pass through either the first or second cation selective membranes into the respective first or second recovery compartments. The onium cations combine with hydroxide ions formed at the cathode or the anion side of the first bipolar membrane 34 to produce the desired onium hydroxide. Impurities such as chloride ion, formate anions and carbonate anions are attracted to the anode and thus remain in the feed compartments 38 and 40. Purified onium hydroxide is formed and recovered from the first and second recovery compartments.

Figure 4:
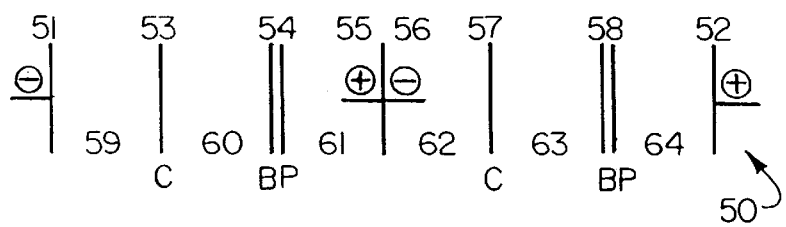
FIG. 4 is a schematic representation of an electrolytic cell containing a stack of two units of the unit cell of FIG. 1 in a bipolar configuration.

An embodiment of an electrochemical cell is illustrated in FIG. 4, which is a schematic representation of an electrochemical cell 50 containing a first cathode 51, a first anode 52 and a polyunit cell containing in sequence beginning at the first cathode 51, a first cation selective membrane 53, a first bipolar membrane 54, a second anode 55, a second cathode 56, a second cation selective membrane 57, and a second bipolar membrane 58. The bipolar membranes 54 and 58 have an anion selective side (not shown) facing the anode and a cation selective side (not shown) facing the cathode. The electrochemical cell 50 contains six compartments; namely, a first feed compartment 60, a first recovery compartment 59, a first water compartment 61, a second feed compartment 63, a second recovery compartment 62 and a second water compartment 64.

In operation of the electrochemical cell illustrated in FIG. 4, a solution containing a liquid electrolyte is charged to the water compartments 61 and 64 and the recovery compartments 59 and 62. A solution containing an onium hydroxide and/or an onium salt is fed to the feed compartments 60 and 63. An electrical potential is established and maintained between the anode and the cathode to produce a flow of current across the cell whereupon the onium cations are attracted toward the respective cathodes and pass through either the first or second cation selective membranes into the respective first or second recovery compartments. The onium cations combine with hydroxide ions formed at the cathodes to produce the desired onium hydroxide. Impurities such as chloride ion, formate anions and carbonate anions are attracted to the anode and thus remain in the feed compartments 60 and 63. Purified onium hydroxide is formed and recovered from the first and second recovery compartments.

Figure 5:
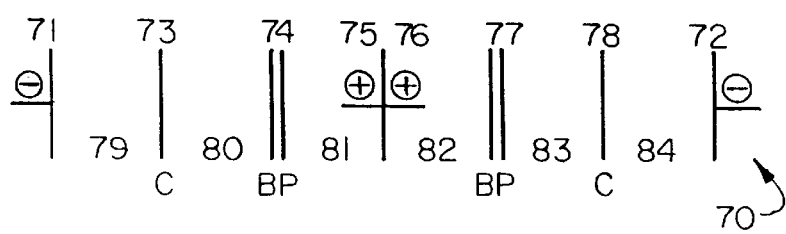
FIG. 5 is a schematic representation of an electrolytic cell containing a stack of two units of the unit cell of FIG. 1 in a monopolar configuration.

An embodiment of an electrochemical cell is illustrated in FIG. 5, which is a schematic representation of an electrochemical cell 70 containing a first cathode 71, a second cathode 72 and a polyunit cell containing in sequence beginning at the first cathode 71, a first cation selective membrane 73, a first bipolar membrane 74, a first anode 75, a second anode 76, a second bipolar membrane 77, and a second cation selective membrane 78. The bipolar membranes 74 and 77 have an anion selective side (not shown) facing the anode and a cation selective side (not shown) facing the cathode. The electrochemical cell 70 contains six compartments; namely, a first feed compartment 80, a first recovery compartment 79, a first water compartment 81, a second feed compartment 83, a second recovery compartment 84 and a second water compartment 82.

In operation of the electrochemical cell illustrated in FIG. 5, a solution containing a liquid electrolyte is charged to the water compartments 81 and 82 and the recovery compartments 79 and 84. A solution containing an onium hydroxide and/or an onium salt is fed to the feed compartments 80 and 83. An electrical potential is established and maintained between the anode and the cathode to produce a flow of current across the cell whereupon the onium cations are attracted toward the respective cathodes and pass through either the first or second cation selective membranes into the respective first or second recovery compartments. The onium cations combine with hydroxide ions formed at the cathodes to produce the desired onium hydroxide. Impurities such as chloride ion, formate anions and carbonate anions are attracted to the anode and thus remain in the feed compartments 80 and 83. Purified onium hydroxide is formed and recovered from the first and second recovery compartments.

Figure 6:
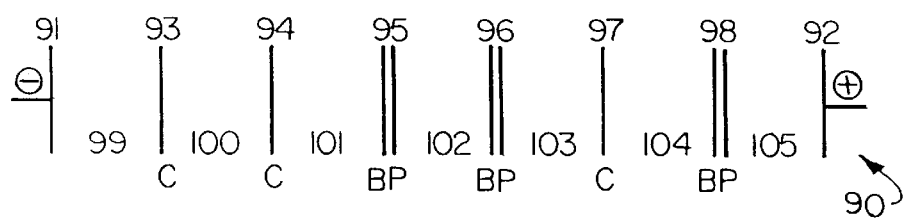
FIG. 6 is a schematic representation of a seven compartment electrodialytic cell in accordance with the invention.

An embodiment of an electrochemical cell is illustrated in FIG. 6, which is a schematic representation of an electrochemical cell 90 containing a cathode 91, an anode 92 and a unit cell containing in sequence beginning at the cathode 91, a first cation selective membrane 93, a second cation selective membrane 94, a first bipolar membrane 95, a second bipolar membrane 96, a third cation selective membrane 97, and a third bipolar membrane 98. The bipolar membranes 95, 96 and 98 have an anion selective side (not shown) facing the anode and a cation selective side (not shown) facing the cathode. The electrochemical cell 90 contains seven compartments; namely, a first feed compartment 101, a purge compartment 100, a first recovery compartment 99, a buffer compartment 102, a second feed compartment 104, a water compartment 105, and a second recovery compartment 103.

In operation of the electrochemical cell illustrated in FIG. 6, a solution containing a liquid electrolyte is charged to the water compartment, the buffer compartment, the purge compartment, and the recovery compartments. A solution containing an onium hydroxide and/or an onium salt is fed to the feed compartments 101 and 104. An electrical potential is established and maintained between the anode and the cathode to produce a flow of current across the cell whereupon the onium cations are attracted toward the cathode and pass through the respective purge compartment and/or respective cation selective membranes into one of the respective recovery compartments. The onium cations combine with hydroxide ions formed at either the cathode or the second bipolar membrane to produce the desired onium hydroxide. Impurities such as chloride ion, formate anions and carbonate anions are attracted to the anode and thus remain in the feed compartments 101 and 104. Purified onium hydroxide is formed and recovered from the recovery compartments 99 and 103.

Figure 7:
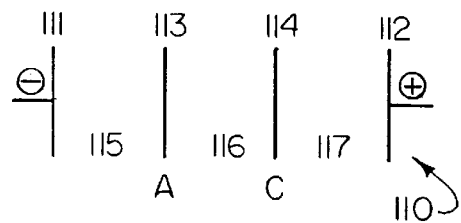
FIG. 7 is a schematic representation of a three compartment secondary electrochemical cell in accordance with the invention.

An embodiment of a second electrochemical cell is illustrated in FIG. 7, which is a schematic representation of an electrochemical cell 110 containing a cathode 111, an anode 112 and a unit cell containing in sequence beginning at the cathode 111, an anion selective membrane 113, and a cation selective membrane 114. The electrochemical cell 110 contains three compartments; namely, a feed-recovery compartment 115, a waste compartment 116 and an anolyte compartment 117.

In operation of the electrochemical cell illustrated in FIG. 7, a solution containing a liquid electrolyte is charged to the waste compartment 116 and the anolyte compartment 117. A solution is transferred from the feed compartment of any of the electrochemical cells of FIGS. 1 to 6 (containing an onium salt and an undesirable amount of acid) to the feed-recovery compartment 115. An electrical potential is established and maintained between the anode and the cathode to produce a flow of current across the cell whereupon anions including undesirable anions are attracted toward the anode 112 and pass through the anion selective membrane 113 into the waste compartment 116. The onium cations may combine with hydroxide ions formed at the cathode to produce the desired onium hydroxide and/or remain in the feed-recovery compartment. Solution from the feed-recovery compartment is then transferred back to the feed compartment of the electrochemical cell from which it was obtained.

Figure 8:
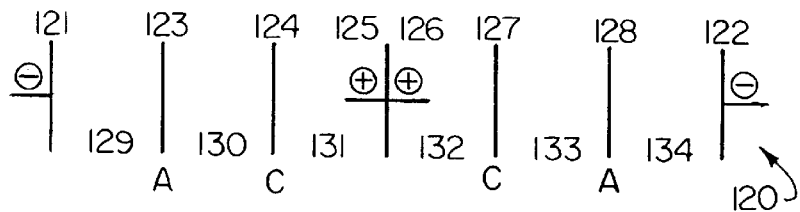
FIG. 8 is a schematic representation of a secondary electrolytic cell containing a stack of two units of the unit cell of FIG. 7 in a monopolar configuration.

An embodiment of a second electrochemical cell is illustrated in FIG. 8, which is a schematic representation of a polyunit electrochemical cell 120 containing a first cathode 121, a second cathode 122 and a polyunit cell containing in sequence beginning at the first cathode 121, a first anion selective membrane 123, a first cation selective membrane 124, a first anode 125, a second anode 126, a second cation selective membrane 127, and a second anion selective membrane 128. The electrochemical cell 120 contains six compartments; namely, a first feed-recovery compartment 129, a first waste compartment 130, a first anolyte compartment 131, a second anolyte compartment 132, a second waste compartment 133 and a second feed-recovery compartment 134.

In operation of the electrochemical cell illustrated in FIG. 8, a solution containing a liquid electrolyte is charged to the first and second waste compartments 130 and 133 and the first and second anolyte compartments 131 and 132. A solution is transferred from the feed compartment of any of the electrochemical cells of FIGS. 1 to 6 (containing an onium salt and an undesirable amount of acid) to the first and second feed-recovery compartments 129 and 134. An electrical potential is established and maintained between the anode and the cathode to produce a flow of current across the cell whereupon anions including undesirable anions are attracted toward the first and second anodes 125 and 126 and pass through the respective first or second anion selective membrane 123 or 128 into either the first or second waste compartment 130 or 133. The onium cations may combine with hydroxide ions formed at the cathode to produce the desired onium hydroxide and/or remain in the feed-recovery compartment. Solution from the feed-recovery compartment is then transferred back to the feed compartment of the electrochemical cell from which it was obtained.

Figure 9:
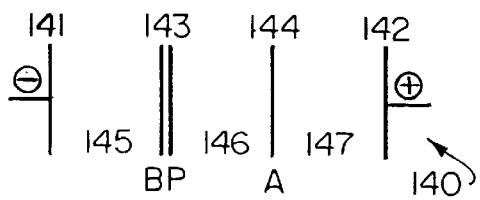
FIG. 9 is a schematic representation of another three compartment secondary electrochemical cell in accordance with the invention.

An embodiment of a second electrochemical cell is illustrated in FIG. 9, which is a schematic representation of an electrochemical cell 140 containing a cathode 141, an anode 142 and a unit cell containing in sequence beginning at the cathode 141, a bipolar membrane 143 and an anion selective membrane 144. The bipolar membrane 143 has an anion selective side (not shown) facing the anode and a cation selective side (not shown) facing the cathode. The electrochemical cell 110 contains three compartments; namely, a feed-recovery compartment 146, a waste compartment 147 and a catholyte compartment 145.

In operation of the electrochemical cell illustrated in FIG. 9, a solution containing a liquid electrolyte is charged to the waste compartment 147 and the catholyte compartment 145. A solution is transferred from the feed compartment of any of the electrochemical cells of FIGS. 1 to 6 (containing an onium salt and an undesirable amount of acid) to the feed-recovery compartment 146. An electrical potential is established and maintained between the anode and the cathode to produce a flow of current across the cell whereupon anions including undesirable anions are attracted toward the anode 142 and pass through the anion selective membrane 144 into the waste compartment 147. The onium cations may combine with hydroxide ions formed at the anion side of the bipolar membrane to produce the desired onium hydroxide and/or remain in the feed-recovery compartment. Solution from the feed-recovery compartment is then transferred back to the feed compartment of the electrochemical cell from which it was obtained.

Figure 10:
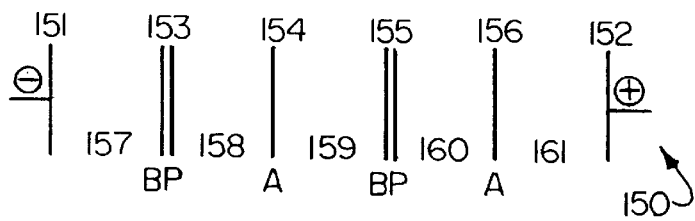
FIG. 10 is a schematic representation of a secondary electrodialytic cell containing a stack of two units of the unit cell of FIG. 9 in accordance with the invention.

An embodiment of a second electrochemical cell is illustrated in FIG. 10, which is a schematic representation of an electrochemical cell 150 containing a cathode 151, an anode 152 and a unit cell containing in sequence beginning at the cathode 151, a first bipolar membrane 153, a first anion selective membrane 154, a second bipolar membrane 155 and a second anion selective membrane 156. The bipolar membranes 153 and 155 have an anion selective side (not shown) facing the anode and a cation selective side (not shown) facing the cathode. The electrochemical cell 150 contains five compartments; namely, a first feed-recovery compartment 158, a first waste compartment 159, a catholyte compartment 157, a second feed-recovery compartment 160, and a second waste compartment 161.

In operation of the electrochemical cell illustrated in FIG. 10, a solution containing a liquid electrolyte is charged to the waste compartments 159 and 161 and the catholyte compartment 157. A solution is transferred from the feed compartment of any of the electrochemical cells of FIGS. 1 to 6 (containing an onium salt and an undesirable amount of acid) to the feed-recovery compartments 158 and 160. An electrical potential is established and maintained between the anode and the cathode to produce a flow of current across the cell whereupon anions including undesirable anions are attracted toward the anode 152 and pass through either the first or second anion selective membrane 154 or 156 into the first or second waste compartment 159 or 161. The onium cations may combine with hydroxide ions formed at the anion side of the first or second bipolar membrane to produce the desired onium hydroxide and/or remain in the first or second feed-recovery compartment. Solution from the first and second feed-recovery compartments is then transferred back to the feed compartment of the electrochemical cell from which it was obtained.

Figure 11:
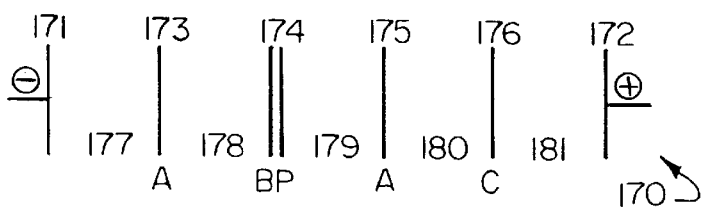
FIG. 11 is a schematic representation of a five compartment secondary electrochemical cell in accordance with the invention.

An embodiment of a second electrochemical cell is illustrated in FIG. 11, which is a schematic representation of an electrochemical cell 170 containing a cathode 171, an anode 172 and a unit cell containing in sequence beginning at the cathode 171, a first anion selective membrane 173, a bipolar membrane 174, a second anion selective membrane 175, and a cation selective membrane 176. The bipolar membrane 174 has an anion selective side (not shown) facing the anode and a cation selective side (not shown) facing the cathode. The electrochemical cell 170 contains five compartments; namely, a first feed-recovery compartment 177, a first waste compartment 178, a second feed-recovery compartment 179, a second waste compartment 180, and an anolyte compartment 181.

In operation of the electrochemical cell illustrated in FIG. 11, a solution containing a liquid electrolyte is charged to the waste compartments 178 and 180 and the anolyte compartment 181. A solution is transferred from the feed compartment of any of the electrochemical cells of FIGS. 1 to 6 (containing an onium salt and an undesirable amount of acid) to the feed-recovery compartments 177 and 179. An electrical potential is established and maintained between the anode and the cathode to produce a flow of current across the cell whereupon anions including undesirable anions are attracted toward the anode 172 and pass through either the first or second anion selective membrane 173 or 175 into the first or second waste compartment 178 or 180. The onium cations may combine with hydroxide ions formed at the cathode or the anion side of the bipolar membrane to produce the desired onium hydroxide and/or remain in the first or second feed-recovery compartment. Solution from the first and second feed-recovery compartments is then transferred back to the feed compartment of the electrochemical cell from which it was obtained.

Figure 12:
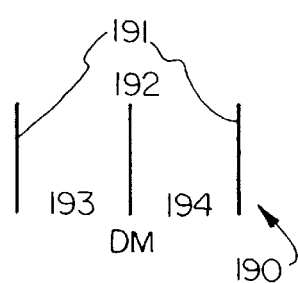
FIG. 12 is a schematic representation of a two compartment secondary diffusion dialysis cell in accordance with the invention.

An embodiment of a diffusion dialysis cell is illustrated in FIG. 12, which is a schematic representation of a diffusion dialysis cell 190 containing a cell frame 191 and a diffusion dialysis membrane 192. The diffusion dialysis cell 190 contains two compartments; namely, a charge-recovery compartment 193 and a permeate compartment 194.

In operation of the diffusion dialysis cell illustrated in FIG. 12, water is charged to the permeate compartment 194. A solution is transferred from the feed compartment of any of the electrochemical cells of FIGS. 1 to 6 (containing an onium salt and an undesirable amount of acid) to the charge-recovery compartment 193. Hydrogen ions and other small undesirable ions migrate through the diffusion dialysis membrane 192 into the permeate compartment 194. The onium cations remain in the charge-recovery compartment 193. Solution from the charge-recovery compartment is then transferred back to the feed compartment of the electrochemical cell from which it was obtained.

Operation of the process of the present invention utilizing the electrochemical cells illustrated in FIGS. 1 to 6 may be batchwise but generally is continuous and all of the liquids may be continuously recirculated. In each of the embodiments, a solution of an onium salt and/or onium hydroxide is charged to the compartment of each unit cell formed by an bipolar membrane and a cation selective membrane. Stated another way, the solution of the onium salt and/or onium hydroxide is charged to the compartment which is between the bipolar membrane and the cation selective membrane in each unit cell. The concentration of the onium salt in the aqueous solution charged to the cell is from about 3% to about 55% by weight and more often between 5% and 40% by weight.

Various materials can be used as anodes in the electrochemical cells. For example, the anode may be made of metals such as titanium-coated electrodes, graphite, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides comprising at least one oxide or mixed oxides of a noble metal such as platinum, iridium, ruthenium, palladium or rhodium.

The cathodes in the electrochemical cells utilized in the process of the present invention comprise stainless steel, nickel, titanium, graphite or carbon steel (iron).

The dividers or separators which can be utilized in the present invention can be selected from a wide variety of microporous diffusion barriers, screens, filters, diaphragms, etc., which contain pores of the desired size to allow the onium cations to migrate toward the cathode. The microporous dividers can be prepared from various materials including plastics such as polyethylene, polypropylene and Teflon which is a polytetrafluoroethylene, ceramics, etc. Specific examples of commercially available microporous separators include: Celanese Celgard and Norton Zitex. Microporous separators are particularly useful when the process of the present invention is utilized to prepare the higher molecular weight hydroxides such as tetra n-butyl phosphonium hydroxide and tetra n-butyl ammonium hydroxide.

The cation selective membranes used in the cells and the process of the invention may be any of those which have been used in the electrolysis of onium salts to onium hydroxides. Preferably, the cation-exchange membranes should comprise a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic and/perfluorocarboxylic acid, perfluorocarbon polymer membranes such as sold by the E. I. dupont Nemours & Co. under the general trade designation "Nafion" such as DuPont's Cationic Nafion 902 membrane, Nafion 969 membrane, and Nafion 423 membrane. Other suitable cation selective membranes include styrenedivinyl benzene copolymer membranes containing cation selective groups such as sulfonate groups, carboxylate groups, etc. Raipore Cationic R1010, (from Pall RAI), Neosepta CMH and Neosepta CM1 membranes from Tokuyama Soda and Flemion FCC from Asahi Glass are useful, some of these particularly with the higher molecular weight quaternary salts. The preparation and structure of cation selective membranes are described in the chapter entitled "Membrane Technology" in *Encyclopedia of Chemical Technology,* Kirk-Othmer, Third Ed., Vol. 15, pp. 92–131, Wiley & Sons, New York, 1985. These pages are hereby incorporated by reference for their disclosure of various cation selective membranes which can be useful in the process of the present invention.

Any anion selective membrane may be utilized in some embodiments including membranes used in processes for the desalination of brackish water. Preferably, membranes should be selective with respect to the particular anions present in the cell (e.g., halide ions). The preparation and structure of anionic membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various anionic membranes which may be useful in some embodiments of the process of the present invention.

Among the anion selective membranes which may be utilized in some embodiments and which are commercially available are the following: Amflon, Series 310, based on fluorinated polymer substituted with quaternary ammonium groups produced by American Machine and Foundry Company; Ionac MA 3148, MA 3236 and MA 3475, based on polymer substituted with quaternary ammonium derived from heterogenous polyvinylchloride produced by Ritter-Pfaulder Corp., Permutit Division; Tosflex IE-SF 34 or IE-SA 48 made by Tosoh Corp. which is a membrane designed to be stable in alkaline media; Neosepta AMH, Neosepta ACM, Neosepta AFN, Neosepta AFX or Neosepta ACLE-SP from Tokuyama Soda Co.; and Selemion AMV and Selemion AAV from Asahi Glass.

One of the advantages of the process of the present invention is that the process in some embodiments leads to the production of HCl rather than $Cl_2$ gas. The bipolar membrane utilized in the process of the present invention prevents the chloride anion from approaching the anode and thereby prevents chlorine gas formation. In the embodiment of FIGS. 2 and 6, higher purity onium hydroxide is obtained since the onium cation passes through two cation selective membranes resulting in lower contamination of the desired hydroxide by other anions such as chloride ion, formate anions and carbonate anions.

The bipolar membranes used in the electrochemical cells are composite membranes comprising three parts: a cation selective side or region, an anion selective side or region, and an interface between the two regions. When a direct current passes across a bipolar membrane, with the cation selective side toward or facing the cathode, electrical conduction is achieved by the transport of $H^+$ and $OH^-$ ions which are produced by the dissociation of water which occurs at the interface under the influence of an electrical field. Bipolar membranes are described, for example, in U.S. Pat. Nos. 2,829,095, 4,024,043 (single film bipolar membranes) and in U.S. Pat. No. 4,116,889 (cast bipolar membranes). The bipolar membranes useful in the process of the present invention include Neosepta Bipolar 1 by Tokuyama Soda, WSI Bipolar, and Aqualytics Bipolar membranes.

Diffusion dialysis membranes utilized in the diffusion dialysis cells include any divider which prevents the passage therethrough of onium cations while permitting the passage of undesirables such as acid compounds, impurities and other contaminants. The identity of the diffusion dialysis membrane varies depending upon the undesirables present in the solution charged to the diffusion dialysis cell. Examples include any of the anion selective membranes mentioned above and Neosepta AFN and AFX.

The current which is passed through the electrochemical cells generally is a current of a voltage dictated by the design and performance characteristics of a given cell which are readily apparent to those skilled in the art and/or can be determined by routine experimentation, Current densities between about 10 and about 500 $mA/cm^2$ are generally used, and current densities between about 50 and about 200 $mA/cm^2$ are preferred. Higher or lower current densities can be used for certain specific applications.

During the electrochemical process, it is generally desirable that the temperature of the liquids within the cells be maintained within the range of from about 10° C. to about 70° C. and more generally, the temperature is maintained at about 50° C. during the electrochemical process.

The following examples illustrate the process of the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

A primary electrochemical cell is assembled according to FIG. 2. The cell contains an anode made of titanium coated with ruthenium oxide having a surface area of 100 $cm^2$, a cathode made of nickel having a surface area of 100 $cm^2$, a bipolar membrane available from Tokuyama Soda Co., and the cation selective membranes are identified as Nafion 902 available from DuPont. A secondary electrochemical cell is provided according to FIG. 7. The secondary electrochemical cell contains an anode made of titanium coated with ruthenium oxide having a surface area of 81 $cm^2$, a cathode made of stainless steel having a surface area of 81 $cm^2$, a Neosepta ACM anion selective membrane available from Tokuyama Soda Co. and a Nafion 423 cation selective membrane available from DuPont. A 1.1 L solution of 1.18M TMAH is charged to the water compartment of the primary cell. A 8.5 L solution of 1.36M TMCl (tetramethylammonium chloride) is charged to the feed compartment of the primary cell. A 1.3 L solution of 1.677M TMAH is charged to the purge compartment of the primary cell while a 8 L solution of 2.22M TMAH is charged to the recovery compartment of the primary cell. A 13 L solution of 1.14M HCl is charged to the waste compartment of the secondary cell while a solution of 1.1M $HNO_3$ is charged to the anolyte compartment of the secondary cell. Solution from the feed compartment of the primary cell is circulated to the feed-recovery compartment of the secondary cell. A current is applied at 5 amps (50 $mA/cm^2$) and a voltage of 11.75 volts to the primary cell and at 7 amps (86.4 $mA/cm^2$) and a voltage of 5.5 volts to the secondary cell. Deionized water may be added to the compartments as needed. After about 43 hours, 10 L of 2.37M TMAH containing less than 5 ppm chloride is obtained from the recovery compartment of the primary cell while 14 L of 1.51M HCl is recovered from the waste compartment of the secondary cell. A current efficiency of 74.8% for the primary cell is achieved while 57.5% for the secondary cell is achieved. The HCl solution may be reused if desired.

EXAMPLE 2

The primary electrochemical cell of Example 1 is used with a secondary electrochemical cell according to FIG. 11. The secondary electrochemical cell contains an anode made of titanium coated with ruthenium oxide having a surface area of 100 $cm^2$, a cathode made of nickel having a surface area of 100 $cm^2$, a Nafion 969 cation selective membrane, a bipolar membrane available from Tokuyama Soda Co., and two Neosepta ACM anion selective membranes. A solution of 5.5 L of 1.5M TMCl is circulated through the feed compartment of the primary cell and the feed-recovery compartments of the secondary cell. A solution of 1.7 L of 0.94M TMAH is charged to the water compartment, a solution of 2.5 L of 1.69M TMAH is charged to the purge compartment, and 14 L of 1.97M TMAH is charged to the recovery compartment of the primary cell. A solution of 16 L of 1.59M HCl is charged to the waste compartments, and a solution of 1.6 L of 0.94M $HNO_3$ is charged to the anolyte compartment of the secondary cell. A current is applied at 5 amps (50 $mA/cm^2$) and a voltage of 14 volts to the primary cell and at 3.5 amps (35 $mA/cm^2$) and a voltage of 6.5 volts to the secondary cell. Deionized water may be added to the compartments as needed. After about 91.75 hours, 19.5 L of 2.1M TMAH containing less than 5 ppm chloride is obtained from the recovery compartment of the primary cell while 23 L of 1.76M HCl is recovered from the waste compartments of the secondary cell. A current efficiency of 78.9% for the primary cell is achieved while 97.8% for the secondary cell is achieved. The HCl solution may be reused if desired.

EXAMPLE 3

The primary electrochemical cell of Example 1 is provided (a secondary electrochemical cell is not used) and the same solutions are charged to the primary electrochemical cell except that a solution of 10 L of 2.0M tetramethylammonium bicarbonate is charged to the feed compartment. A current is applied at 5 amps (50 $mA/cm^2$) and at a voltage of 12 volts. After about 52 hours, a 10.5 L solution of 2.32M TMAH is recovered from the recovery compartment. A current efficiency of 73.6% is achieved.

EXAMPLE 4

An electrochemical cell according to FIG. 1 is provided. The cell contains an anode made of titanium coated with ruthenium oxide having a surface area of 81 $cm^2$, a cathode made of stainless steel having a surface area of 81 $cm^2$, a Tokuyama Soda Co. bipolar membrane and a Nafion 902 cation selective membrane. A diffusion dialysis cell according to FIG. 12 is also provided. The diffusion dialysis cell contains a Neosepta AFX anion exchange membrane having an effective surface area of 90 $cm^2$ as a diffusion dialysis membrane. A solution of 3 L of 1.1M TMCl is circulated between the feed compartment of the electrochemical cell and the charge-recovery compartment of the diffusion dialysis cell. A 1 L solution of 1.06M TMAH is charged to the water compartment and a 0.5 L solution of 1.91M TMAH is charged to the recovery compartment of the electrochemical cell. A 5 L solution of deionized water is charged to the permeate compartment of the diffusion dialysis cell at a flow rate of 0.01 L/min. A current is applied at 5 amps (61.7 $mA/cm^2$) and at a voltage of 13.25 volts to the electrochemical cell. After about 10 hours, a 0.95 L solution of 2.35M TMAH is recovered from the recovery compartment. A current efficiency of 71.1% is achieved.

EXAMPLE 5

The primary and secondary electrochemical cells of Example 1 are provided. A solution of 11 L of 1M TEAH is circulated through the feed compartment of the primary cell and the feed-recovery compartment of the secondary cell. A solution of 1 L of 0.8M TEAH is charged to the water compartment, a solution of 1.3 L of 1M TEAH is charged to purge compartment, and a solution of 8 L of 1.4M TEAH to the recovery compartment of the primary cell. A solution of 13 L of 1M HCl is charged to the waste compartment and a solution of 1.3M $H_2SO_4$ is charged to the anolyte compartment of the secondary cell. A current is applied at 5 amps (50 $mA/cm^2$) and a voltage of 12.5 volts to the primary cell and at 7 amps (86.4 $mA/cm^2$) and a voltage of 6.8 volts to the secondary cell. Deionized water may be added to the compartments as needed. After about 43 hours, 10 L of 1.4M TEAH containing less than 0.1 ppm chloride is obtained from the recovery compartment of the primary cell while 14 L of 1.3M HCl is recovered from the waste compartment of the secondary cell. A current efficiency of 69% for the primary cell is achieved while 56% for the secondary cell is achieved. The HCl solution may be reused if desired.

EXAMPLE 6

An electrochemical cell according to FIG. 1 is provided. The electrochemical cell contains an anode of titanium coated with ruthenium oxide having a surface area of 100 $cm^2$, a cathode made of stainless steel having a surface area of 100 $cm^2$, a bipolar membrane from Tokuyama Soda Co., and a Flemion FCC cation selective membrane from Asahi Glass. A solution of 13 L of 1.35M tetramethylammonium carbonate is charged to the feed compartment while a solution of 2.3 L of 0.8M TMAH is charged to the water compartment, and deionized water containing 2% by weight of TMAH is charged to the recovery compartment. A current is applied at 5 amps (50 $mA/cm^2$) and at a voltage of 9 volts. A solution of 2.4M TMAH containing 16 ppm carbonate ions is recovered from the recovery compartment. A current efficiency of 85% is achieved.

EXAMPLE 7

The electrochemical cell according to Example 6 is provided. A solution of 10 L of 2.2M tetramethylammonium formate is charged to the feed compartment while a solution of 0.75M TMAH is charged to the water compartment while deionized water containing 2% by weight of TMAH is charged to the recovery compartment. A current is applied at 7.5 amps (75 mA/cm$^2$) and at a voltage of 10.5 volts. A solution of 2.1M TMAH containing 3 ppm formate ions is recovered from the recovery compartment. A current efficiency of 84% is achieved. Excess formic acid which may form in the feed compartment may be removed by distilling solution transferred from the feed compartment. The formic acid solution may be reused if desired.

EXAMPLE 8

The primary and secondary electrochemical cells of Example 1 are provided. A solution of 0.75M tetrabutylphosphonium chloride is circulated through the feed compartment from the primary electrochemical cell and the feed-recovery compartment of the secondary electrochemical cell. A solution of 0.8M tetrabutylphosphonium hydroxide is charged to the water compartment and the purge compartment of the primary electrochemical cell. A solution of 1.3M HCl is charged to the waste compartment of the secondary electrochemical cell. A solution of 0.5M of $H_2SO_4$ is charged to the anolyte compartment of the secondary electrochemical cell. Deionized water containing 2% by weight of tetrabutylphosphonium hydroxide is charged to the recovery compartment of the primary electrochemical cell. A current is applied at 5 amps (50 mA/cm$^2$) and a voltage of 12 volts to the primary cell and at 7 amps (86.4 mA/cm$^2$) and a voltage of 5.5 volts to the secondary cell. Deionized water may be added to the compartments as needed. After about 43 hours, 10 L of 1.1M tetrabutylphosphonium hydroxide containing less than 0.1 ppm chloride is obtained from the recovery compartment of the primary cell while 14 L of 1.51M HCl is recovered from the waste compartment of the secondary cell. A current efficiency of 68% for the primary cell is achieved while 53% for the secondary cell is achieved. The HCl solution may be reused if desired.

EXAMPLE 9

An electrochemical cell according to FIG. 2 is provided. The electrochemical cell contains an anode of titanium coated with ruthenium oxide having a surface area of 100 cm$^2$, a cathode made of nickel having a surface area of 100 cm$^2$, a bipolar membrane from Tokuyama Soda Co., and two Flemion FCC cation selective membranes from Asahi Glass. A solution of 1.5M of tetramethylammonium carbonate in methanol is charged to the feed compartment, a solution of 1M TMAH in methanol is introduced into the water and purge compartments, and a solution of methanol containing 2% TMAH is charged into the recovery compartment. A current is applied at 5 amps (50 mA/cm$^2$) and a voltage of 12 volts. A solution of 2.2M TMAH containing 1 ppm carbonate ions is recovered from the recovery compartment. A current efficiency of 65% is achieved.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for preparing onium hydroxide from a corresponding onium salt and for purifying onium hydroxide comprising:

(A) providing an electrochemical cell comprising a cathode, an anode, a divider and a bipolar membrane, the bipolar membrane having an anion selective side facing the anode and a cation selective side facing the cathode, wherein the divider is positioned between the cathode and the bipolar membrane, and the bipolar membrane is positioned between the divider and the anode, thereby defining a feed compartment between the divider and the bipolar membrane, a recovery compartment between the divider and the cathode, and a water compartment between the bipolar membrane and the anode;

(B) charging a solution comprising at least one of the onium salt and the onium hydroxide to be purified to the feed compartment;

(C) charging a liquid electrolyte to the other compartments;

(D) passing a current through the electrochemical cell to produce the onium hydroxide in the recovery compartment; and (E) recovering the onium hydroxide from the recovery compartment.

2. The process of claim 1, wherein the electrochemical cell does not contain an anion selective membrane.

3. The process of claim 1, wherein the divider is a cation selective membrane.

4. The process of claim 3, wherein the electrochemical cell further comprises a second cation selective membrane positioned between the cation selective membrane and the cathode, thereby defining a purge compartment between the cation selective membrane and the second cation selective membrane, wherein a liquid electrolyte is charged to the purge compartment.

5. The process of claim 1, wherein the divider is a first cation selective membrane and the electrochemical cell further comprises a second cation selective membrane positioned between the bipolar membrane and the anode, and a second bipolar membrane positioned between the second cation selective membrane and the anode, the second bipolar membrane having an anion selective side facing the anode and a cation selective side facing the cathode, thereby defining a first feed compartment between the bipolar membrane and the first cation selective membrane, a first recovery compartment between the first cation selective membrane and the cathode, a second feed compartment between the second bipolar membrane and the second cation selective membrane, a second recovery compartment between the second cation selective membrane and the bipolar membrane, and a water compartment between the second bipolar membrane and the anode, wherein a liquid electrolyte is charged to each recovery and water compartment and the solution of the onium salt or the onium hydroxide to be purified is charged to each feed compartment.

6. The process of claim 1, wherein the onium salt comprises at least one of an onium chloride, an onium formate, an onium carbonate, an onium bicarbonate and an onium alkyl carbonate.

7. The process of claim 1, wherein the onium salt or the onium hydroxide to be purified comprises at least one of an ammonium compound, a phosphonium compound, and a sulfonium compound.

8. The process of claim 1, further comprising:

providing a second electrochemical cell comprising a cathode, an anode, an anion selective membrane and a cation selective membrane, wherein the anion selective membrane is positioned between the cation selective membrane and the cathode, and the cation selective membrane is positioned between the anion selective membrane and the anode, thereby defining a feed-recovery compartment between the cathode and the anion selective membrane, a waste compartment between the anion selective membrane and the cation selective membrane, and an anolyte compartment between the anode and the cation selective membrane;

transferring solution from the feed compartment of the first electrochemical cell into the feed-recovery compartment of the second electrochemical cell, charging a liquid electrolyte to the other compartments and passing a current through the second electrochemical cell thereby increasing the pH of the feed-recovery compartment;

transferring solution from the feed-recovery compartment of the second electrochemical cell back to the feed compartment of the first electrochemical cell.

9. The process of claim 1, further comprising:

providing a second electrochemical cell comprising a cathode, an anode, an anion selective membrane and a bipolar membrane, the bipolar membrane having an anion selective side facing the anode and a cation selective side facing the cathode, wherein the anion selective membrane is positioned between the bipolar membrane and the anode, and the bipolar membrane is positioned between the anion selective membrane and the cathode, thereby defining a feed-recovery compartment between the bipolar membrane and the anion selective membrane, a waste compartment between the anion selective membrane and the anode, and a catholyte compartment between the cathode and the bipolar membrane;

transferring solution from the feed compartment of the first electrochemical cell into the feed-recovery compartment of the second electrochemical cell, charging a liquid electrolyte to the other compartments and passing a current through the second electrochemical cell thereby increasing the pH of the feed-recovery compartment;

transferring solution from the feed-recovery compartment of the second electrochemical cell back to the feed compartment of the first electrochemical cell.

10. The process of claim 1, further comprising providing a second electrochemical cell comprising a cathode, an anode, and an anion selective membrane therebetween, thereby defining a feed-recovery compartment between the cathode and the anion selective membrane, and a waste compartment between the anion selective membrane and the anode;

transferring solution from the feed compartment of the first electrochemical cell into the feed-recovery compartment of the second electrochemical cell, charging a liquid electrolyte to the waste compartment and passing a current through the second electrochemical cell thereby increasing the pH of the feed-recovery compartment;

transferring solution from the feed-recovery compartment of the second electrochemical cell back to the feed compartment of the first electrochemical cell.

11. The process of claim 1, further comprising:

transferring solution from the feed compartment of the electrochemical cell to a diffusion dialysis cell containing a membrane permeable to hydrogen ions whereby a portion of the solution passes through the membrane and another portion does not pass through the membrane, transferring the portion of the solution from the diffusion dialysis cell which did not pass through the membrane back to the feed compartment of the electrochemical cell.

12. The process of claim 1, further comprising:

removing solution from the feed compartment of the electrochemical cell;

distilling the removed solution thereby removing acid therefrom; and transferring the distilled solution back to the feed compartment of the electrochemical cell.

13. The process of claim 12, wherein the onium salt comprises onium formate.

14. The process of claim 1, further comprising:

removing solution from the feed compartment of the electrochemical cell;

passing the removed solution through an ion exchange system; and transferring the solution back to the feed compartment of the electrochemical cell.

15. The process of claim 14, wherein the ion exchange system comprises an anionic exchange resin.

16. A process for preparing an onium hydroxide from a corresponding onium salt comprising:

(A) providing an electrochemical cell comprising a cathode, an anode, a cation selective membrane and a bipolar membrane, the bipolar membrane having an anion selective side facing the anode and a cation selective side facing the cathode, wherein the cation selective membrane is positioned between the cathode and the bipolar membrane, and the bipolar membrane is positioned between the cation selective membrane and the anode, thereby defining a feed compartment between the cation selective membrane and the bipolar membrane, a recovery compartment between the cation selective membrane and the cathode, and a water compartment between the bipolar membrane and the anode;

(B) charging a solution comprising the onium salt to the feed compartment;

(C) charging a liquid electrolyte to the other compartments;

(D) passing a current through the electrochemical cell to produce the onium hydroxide in the recovery compartment; and (E) recovering the onium hydroxide from the recovery compartment.

17. The process of claim 16, wherein the electrochemical cell does not contain an anion selective membrane.

18. The process of claim 16, wherein the onium salt comprises at least one of an onium chloride, an onium formate, an onium carbonate, an onium bicarbonate and an onium alkyl carbonate.

19. The process of claim 16, wherein the onium salt comprises at least one of an ammonium salt, a phosphonium salt, and a sulfonium salt.

20. The process of claim 16, further comprising:

providing a second electrochemical cell comprising a cathode, an anode, an anion selective membrane and a cation selective membrane, wherein the anion selective membrane is positioned between the cation selective membrane and the cathode, and the cation selective membrane is positioned between the anion selective membrane and the anode, thereby defining a feed-recovery compartment between the cathode and the anion selective membrane, a waste compartment between the anion selective membrane and the cation selective membrane, and an anolyte compartment between the anode and the cation selective membrane;

transferring solution from the feed compartment of the first electrochemical cell into the feed-recovery compartment of the second electrochemical cell, charging a liquid electrolyte to the other compartments and passing a current through the second electrochemical cell thereby increasing the pH of the feed-recovery compartment;

transferring solution from the feed-recovery compartment of the second electrochemical cell back to the feed compartment of the first electrochemical cell.

21. The process of claim 16, further comprising:

providing a second electrochemical cell comprising a cathode, an anode, an anion selective membrane and a bipolar membrane, the bipolar membrane having an anion selective side facing the anode and a cation selective side facing the cathode, wherein the anion selective membrane is positioned between the bipolar membrane and the anode, and the bipolar membrane is positioned between the anion selective membrane and the cathode, thereby defining a feed-recovery compartment between the bipolar membrane and the anion selective membrane, a waste compartment between the anion selective membrane and the anode, and a catholyte compartment between the cathode and the bipolar membrane;

transferring solution from the feed compartment of the first electrochemical cell into the feed-recovery compartment of the second electrochemical cell, charging a liquid electrolyte to the other compartments and passing a current through the second electrochemical cell thereby increasing the pH of the feed-recovery compartment;

transferring solution from the feed-recovery compartment of the second electrochemical cell back to the feed compartment of the first electrochemical cell.

22. The process of claim 16, further comprising providing a second electrochemical cell comprising a cathode, an anode, and an anion selective membrane therebetween, thereby defining a feed-recovery compartment between the cathode and the anion selective membrane, and a waste compartment between the anion selective membrane and the anode;

transferring solution from the feed compartment of the first electrochemical cell into the feed-recovery compartment of the second electrochemical cell, charging a liquid electrolyte to the waste compartment and passing a current through the second electrochemical cell thereby increasing the pH of the feed-recovery compartment;

transferring solution from the feed-recovery compartment of the second electrochemical cell back to the feed compartment of the first electrochemical cell.

23. The process of claim 16, further comprising:

transferring solution from the feed compartment of the electrochemical cell to a diffusion dialysis cell containing a membrane permeable to hydrogen ions whereby a portion of the solution passes through the membrane and another portion does not pass through the membrane, transferring the portion of the solution from the diffusion dialysis cell which did not pass through the membrane back to the feed compartment of the electrochemical cell.

24. The process of claim 16, further comprising:

removing solution from the feed compartment of the electrochemical cell;

distilling the removed solution thereby removing acid therefrom; and transferring the distilled solution back to the feed compartment of the electrochemical cell.

25. The process of claim 16, wherein the electrochemical cell comprises, beginning at the cathode, a first cation selective membrane, a second cation selective membrane, a first bipolar membrane, a second bipolar membrane, a third cation selective membrane, and a third bipolar membrane, thereby defining a first recovery compartment between the cathode and the first cation selective membrane, a first purge compartment between the first cation selective membrane and the second cation selective membrane, a first feed compartment between the second cation selective membrane and the first bipolar membrane, a buffer compartment between the first bipolar membrane and the second bipolar membrane, a second recovery compartment between the third cation selective membrane and the second bipolar membrane, a second feed compartment between the third cation selective membrane and the third bipolar membrane, and a water compartment between the anode and the third bipolar membrane, wherein a liquid electrolyte is charged to each purge, water recovery and buffer compartment and the solution comprising the onium salt is charged to each feed compartment.

26. The process of claim 16, further comprising:

removing solution from the feed compartment of the electrochemical cell;

passing the removed solution through an anionic exchange resin; and transferring the solution back to the feed compartment of the electrochemical cell.

27. A process for purifying an onium hydroxide solution comprising:

(A) providing an electrochemical cell comprising a cathode, an anode, a cation selective and a bipolar membrane, the bipolar membrane having an anion selective side facing the anode and a cation selective side facing the cathode, wherein the cation selective membrane is positioned between the cathode and the bipolar membrane, and the bipolar membrane is positioned between the cation selective membrane and the anode, thereby defining a feed compartment between the cation selective membrane and the bipolar membrane, a recovery compartment between the cation selective membrane and the cathode, and a water compartment between the bipolar membrane and the anode;

(B) charging the onium hydroxide solution to the feed compartment;

(C) charging a liquid electrolyte to the other compartments;

(D) passing a current through the electrochemical cell to regenerate onium hydroxide in the recovery compartment; and (E) recovering a purified onium hydroxide solution from the recovery compartment.

28. The process of claim 27, wherein the onium hydroxide comprises an ammonium hydroxide.

29. A process for preparing tetramethylammonium hydroxide from a tetramethylammonium salt and for purifying tetramethylammonium hydroxide comprising:

(A) providing an electrochemical cell comprising a cathode, an anode, a divider and a bipolar membrane, the bipolar membrane having an anion selective side facing the anode and a cation selective side facing the cathode, wherein the divider is positioned between the cathode and the bipolar membrane, and the bipolar membrane is positioned between the divider and the anode, thereby defining a feed compartment between the divider and the bipolar membrane, a recovery compartment between the divider and the cathode, and a water compartment between the bipolar membrane and the anode;

(B) charging a solution comprising at least one of the tetramethylammonium salt and the tetramethylammonium hydroxide to be purified to the feed compartment;

(C) charging a liquid electrolyte to the other compartments;

(D) passing a current through the electrochemical cell to produce the tetramethylammonium hydroxide in the recovery compartment; and (E) recovering the tetramethylammonium hydroxide from the recovery compartment.

30. The process of claim 29, wherein the electrochemical cell does not contain an anion selective membrane.

31. The process of claim 29, wherein the divider is a cation selective membrane.

* * * * *